United States Patent
Ryan et al.

(10) Patent No.: US 6,881,213 B2
(45) Date of Patent: Apr. 19, 2005

(54) DEVICE AND METHOD TO EXPAND TREATMENT ARRAY

(75) Inventors: Thomas P. Ryan, Flemington, NJ (US);
David Y. Yuan, Somerset, NJ (US);
Roddi J. Simpson, Jersey City, NJ (US); Scott A. Ciarrocca, Stockton, NJ (US); Alexander J. Sinton, Doylestown, PA (US)

(73) Assignee: Ethicon, Inc., Somerville, NJ (US)

( * ) Notice: Subject to any disclaimer, the term of this patent is extended or adjusted under 35 U.S.C. 154(b) by 179 days.

(21) Appl. No.: 10/278,235

(22) Filed: Oct. 23, 2002

(65) Prior Publication Data

US 2004/0002748 A1 Jan. 1, 2004

Related U.S. Application Data (63) Continuation-in-part of application No. 10/186,389, filed on Jun. 28, 2002, now abandoned.

(51) Int. Cl.$^7$ .............................................. A61B 18/18
(52) U.S. Cl. ...................................... 606/41; 607/101
(58) Field of Search ...................... 606/41–50; 607/96, 607/101, 102

(56) References Cited

U.S. PATENT DOCUMENTS

| | | | |
|---|---|---|---|
| 5,722,401 A | * 3/1998 | Pietroski et al. | 600/374 |
| 5,769,880 A | 6/1998 | Truckai et al. | |
| 5,817,092 A | 10/1998 | Behl | |
| 5,827,276 A | 10/1998 | Le Veen et al. | |
| 6,050,992 A | 4/2000 | Nichols | |
| 6,123,718 A | * 9/2000 | Tu et al. | 607/113 |
| 6,488,673 B1 | * 12/2002 | Laufer et al. | 604/516 |
| 6,589,238 B2 | * 7/2003 | Edwards et al. | 606/41 |
| 6,625,486 B2 | * 9/2003 | Lundkvist et al. | 604/21 |

* cited by examiner

Primary Examiner—Roy D. Gibson (57) ABSTRACT

A medical device is provided and includes an elongated tube that has a longitudinal axis and an expandable member attached to the tube. The expandable member is expandable from a collapsed configuration to an expanded configuration. A plurality of electrodes is attached to the expandable member. The electrodes are used to emit energy. Each of the electrodes is arranged generally coaxially relative to the tube when the expandable member is in its collapsed and expanded configurations.

25 Claims, 9 Drawing Sheets

DEVICE AND METHOD TO EXPAND TREATMENT ARRAY

CROSS REFERENCE TO RELATED APPLICATION

This application is a continuation-in-part of commonly owned U.S. application Ser. No. 10/186,389, entitled "DEVICE AND METHOD TO EXPAND TREATMENT ARRAY" filed Jun. 28, 2002, now abandoned.

FIELD OF THE INVENTION

The present invention relates to an RF (radio frequency) device for use in the performance of RF thermal treatment of tissue, and more particularly, to an RF device adapted for use during a laparoscopic or percutaneous procedure.

BACKGROUND OF THE INVENTION

During an RF procedure, a probe is placed into a target tissue for treating malignant and nonmalignant conditions. The probe is typically provided with an array of electrodes so that RF energy can be supplied to the target tissue.

Various RF devices have been employed to treat a large volume of tissue with a single applicator in a single procedure. One such device employs an array of wire electrodes that deploys and assumes an inverted umbrella shape after reaching the target tissue. When deployed, the inverted umbrella shape of the electrode array may be altered by tissue mechanical resistance or calcifications such that the electrode array exhibits a non-uniform pattern of thermal treatment. Such a non-uniform pattern is undesirable because tissue effects will be affected by the changing distance between adjacent electrodes that diverge or converge.

An alternative approach involves the use of an array of electrodes that have a large diameter. Such an approach is also undesirable because the large electrode array cannot be inserted through the body unless an open surgery is performed. Further, the large electrode array cannot be accommodated through a laparoscopic trocar that has a small diameter of 5 to 10 mm.

Accordingly, there is a need for an improved RF device having electrodes that deploy in a uniform and parallel manner along the length of the electrodes and that can be accommodated in a laparoscopic trocar having a small diameter.

SUMMARY OF THE INVENTION

In accordance with the present invention, there is provided a medical device used for thermal treatment of tissue. The medical device includes an elongated tube that has a longitudinal axis and an expandable member attached to the tube. The expandable member is expandable from a collapsed configuration to an expanded configuration. A plurality of energy-emitting electrodes is attached to the expandable member. Each of the electrodes is arranged generally coaxially relative to the tube when the expandable member is in its collapsed and expanded configurations.

A method is also disclosed for performing thermal treatment of tissue using the medical device. Initially, the tube is placed near the tissue area with the expandable member in its collapsed configuration. In this step, the electrodes are in close proximity to each other and all of the electrodes are arranged generally co-axially relative to the tube. Then, the expandable member is expanded so that it assumes its expanded configuration. In this step, the electrodes are spaced apart from each other and all of the electrodes are arranged generally coaxially relative to the tube.

Other features and aspects of the present invention will become more fully apparent from the following detailed description of the exemplary embodiment, the appended claims and the accompanying drawings.

BRIEF DESCRIPTION OF THE DRAWINGS

For a more complete understanding of the present invention, reference is made to the following detailed description of the exemplary embodiment considered in conjunction with the accompanying drawings, in which:

FIG. 9b is a top, perspective view of the RF device of FIG. 9a;

DETAILED DESCRIPTION OF THE EXEMPLARY EMBODIMENT

Figures 1, 2, 3:
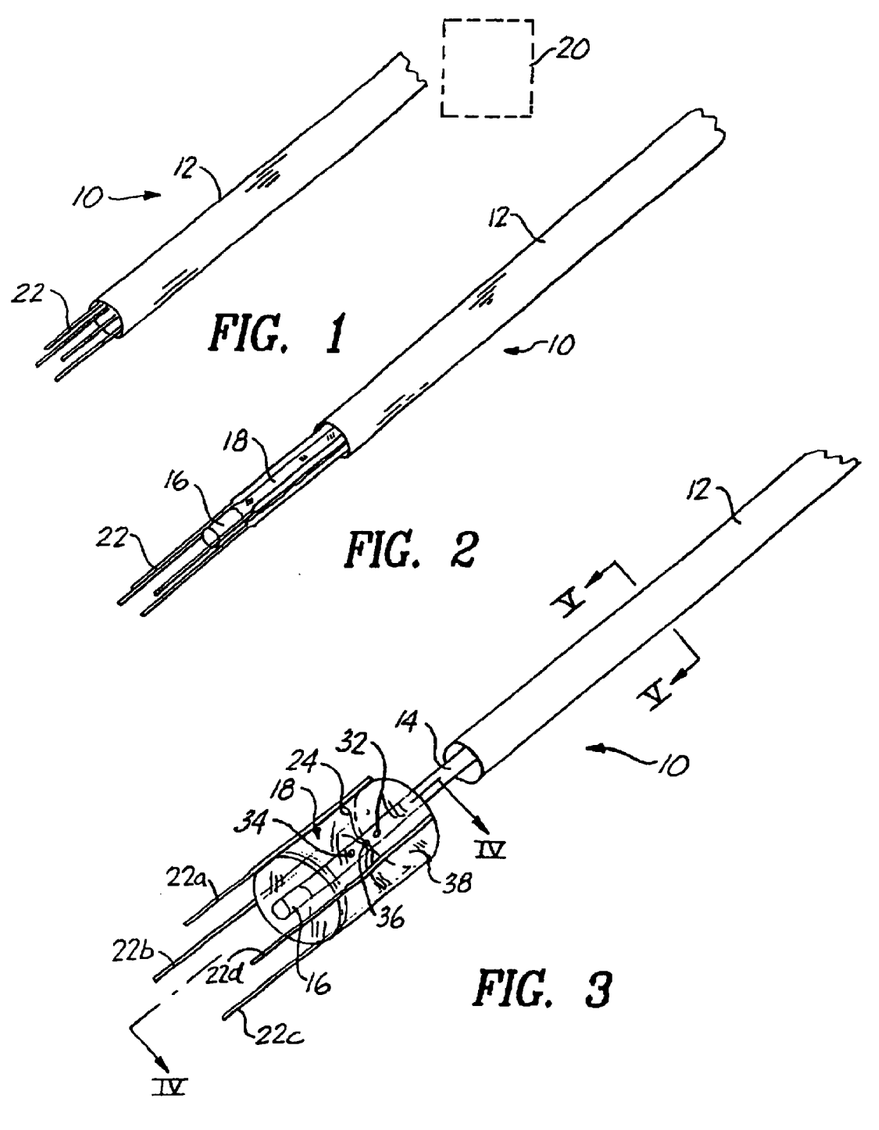
FIG. 1 is a front, perspective view of an RF device constructed in accordance with the present invention, which shows a multi-lumen tube in a retracted position.
FIG. 2 is a view similar to the view shown in FIG. 1, except that the multi-lumen tube is between its retracted and extended positions, and which shows a balloon member in its collapsed configuration.
FIG. 3 is a view similar to the view shown in FIG. 1, except that the multi-lumen tube is in its extended position and the balloon member is in its expanded configuration.

FIG. 1 shows an RF device 10 used for thermal treatment of tissue. The RF device 10 can be applied through 5–10 mm or larger laparoscopic trocar. Alternatively, the RF device 10 can be applied percutaneously to the affected tissue area.

With reference to FIGS. 1 to 3, the RF device 10 includes an outer sheath 12 which is linearly shaped and an elongated multi-lumen tube 14 sized and shaped to be coaxially received within the outer sheath 12. The multi-lumen tube 14 has a longitudinal axis and is also linearly shaped. The multi-lumen tube 14 is also sized and shaped to move relative to the outer sheath 12 by conventional methods such as by laparoscopic surgical tools (e.g., graspers, forceps, retractors) sliding through a plastic or metal trocar. As shown in FIG. 2, the multi-lumen tube 14 has a distal end 16 that can extend from the outer sheath 12. More particularly, the multi-lumen tube 14 is movable between a retracted position (see FIG. 1), in which the multi-lumen tube 14 retracts into the outer sheath 12, and an extended position (see FIG. 3), in which the multi-lumen tube 14 extends from the outer sheath 12. Alternatively, the outer sheath 12 can be sized and shaped to move relative to the multi-lumen tube 14.

Referring to FIG. 3, the RF device 10 further includes a balloon member 18 attached to the multi-lumen tube 14. The tube 14 extends completely through the balloon member 18. More particularly, the balloon member 18 is positioned along an intermediate length of the tube 14. For reasons to be discussed hereinafter, the balloon member 18 is sized and shaped to inflate into a fully expanded configuration as shown in FIG. 3 and to deflate into a fully collapsed configuration as shown in FIG. 2. Further, when the multi-lumen tube 14 is in its retracted position, the balloon member 18 is in its collapsed configuration and compressed within the outer sheath 12 so as to facilitate insertion into a trocar for delivery to the affected tissue area. When the multi-lumen tube 14 is in its extended position, the balloon member 18 is released from the outer sheath 12 such that it can move between its expanded configuration and collapsed configuration.

Figure 4:
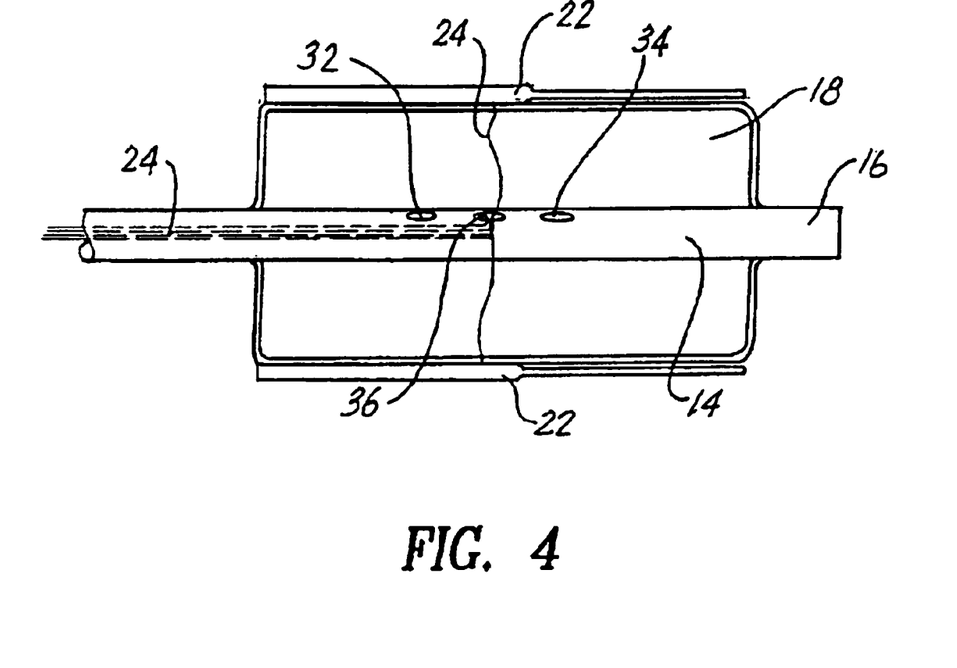
FIG. 4 is a cross-sectional view, taken along section lines IV—IV and looking in the direction of the arrows, of the RF device of FIG. 3.

The RF device 10 is powered by an RF energy source, such as a conventional electrosurgical generator 20 (shown in phantom in FIG. 1). The operating frequency ranges from 100 to 3,000 kHz, preferably 400 to 700 kHz. As illustrated in FIG. 3, the RF device 10 includes a plurality of generally linearly shaped electrode needles 22 for delivering RF energy. The electrode diameters are between 0.25 and 1.0 mm, preferably 0.5 mm. The tips may be beveled, as a hypodermic needle, or other sharp tip. The polarity of the electrode needles 22 can be regulated such that each of the electrode needles 22 can be activated in various arrangements to be used as an active or return electrode. For example, two adjacent electrode needles 22a, 22b may be active and the remaining two electrode needles 22c, 22d may be return. Alternatively, adjacent electrode needles 22a, 22b may be active and return, making an alternating pattern. Alternatively, all electrode needles 22a, 22b, 22c, and 22d may be active and the return is a ground pad on the patient (not shown). Each of the electrode needles 22 is attached to the outer surface of the balloon member 18 by conventional attaching means, such as a solvent-based glue. It will be understood that although four electrode needles 22 are shown in FIG. 3, the number of electrode needles 22 can vary. The electrosurgical generator 20 is electrically connected to the electrode needles 22 and provides monopolar or bipolar energy to them in order to thermally treat tissue. With reference to FIG. 4, a plurality of wire leads 24 extends through the multi-lumen tube 14 and is electrically connected to the electrosurgical generator 20 and to the electrode needles 22. As shown in FIG. 4, each of the electrode needles 22 is attached to one of the wire leads 24. Although the electrode needles 22 may be connected in various bipolar or monopolar configurations, the order of connections may be changed at time intervals to facilitate the distribution of RF energy and configure the heating field dynamically. The electrode needles 22 can be used or can be equipped with components to sense tissue properties, such as either temperature, impedance, or other properties. This sensing may determine what the new order of connections will be to alter the heating pattern based on the sensor feedback. The sensors may be temperature sensing, as in thermistors, thermocouples, or fiber optic sensors and may be located on or inside the electrode needles 22.

When the balloon member 18 is in its collapsed configuration, the electrode needles 22 are in a compressed position, in which the electrode needles 22 are proximate to the multi-lumen tube 14 as shown in FIG. 2 so as to facilitate insertion within the outer sheath 22. Further, as the balloon member 18 inflates to its expanded configuration, the electrode needles 22 move to a deployed configuration, in which the electrode needles 22 move radially outward relative to the multi-lumen tube 14 such that each of the electrode needles 22 extends in a substantially parallel relationship relative to the other electrode needles 22 as shown in FIG. 3. The balloon member 18 expands to a diameter of between 10 and 50 mm, preferably 20 mm if four electrode needles 22a, 22b, 22c, 22d are provided and 30 mm if six electrode needles are provided. After extending, each of the electrode needles 22 is substantially spaced from the other electrode needles 22. Because RF energy is applied to the affected tissue area interstitially, having substantial spacing between the electrode needles 22 facilitates the spread of RF energy deposition, thereby treating a large volume of tissue. The electrode needles 22 are arranged generally coaxially relative to the tube 14 when the balloon member 18 is in its collapsed configuration and its expanded configuration.

Figure 5:
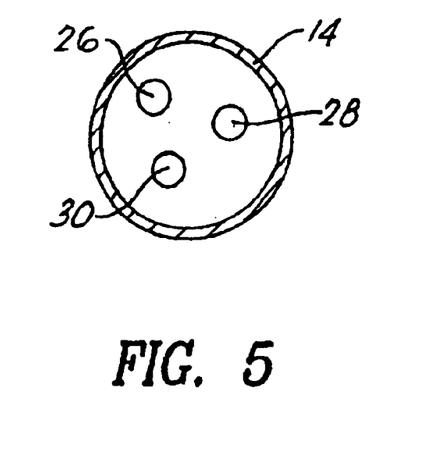
FIG. 5 is a cross-sectional view, taken along section lines V—V and looking in the direction of the arrows, of the RF device of FIG. 3.

With reference to FIG. 5, the multi-lumen tube 14 includes a passageway 26 for receiving air or liquid, either of which can be used to inflate the balloon member 18 (see FIG. 3) to its fully expanded configuration (see FIG. 3). This could be simply done with a syringe. A passageway 28 is also provided for receiving a vacuum to evacuate the air or liquid from the balloon member 18, thereby causing it to deflate and assume its fully collapsed configuration as shown in FIG. 2. This could also be done with a syringe. Alternatively, the multi-lumen tube 14 can employ a single passageway (not shown) that can receive air, fluid, and vacuum, rather than having the two separate passageways 26, 28. Further, a passageway 30 is sized and shaped to allow the wire leads 24 (see FIG. 4) to pass therethrough. The air or liquid may be circulating inside the balloon member 18 to cool the electrode needles 22 and the tissue surface that contacts the electrode needles 22. The electrode needles 22 can incorporate heat pipe technology, typically a sealed hollow cylinder, with conductive fluid, whose purpose is to transport heat away from the hottest segments.

Referring to FIG. 3, the multi-lumen tube 14 includes a vent 32 for receiving air/liquid from the passageway 26 (see FIG. 5), a vent 34 for receiving vacuum from the passageway 28 (see FIG. 5), and a plurality of wire vents 36, each of which is sized and shaped to allow one of the wire leads 24 to pass therethrough and connect to one of the electrode needles 22. The vents 32, 34 and the wire vents 36 are located underneath the balloon member 18.

When inflated as shown in FIG. 3, the balloon member 18 has a substantially cylindrically-shaped configuration and includes an interior chamber 38 filled with air or liquid. The balloon member 18 can be made from a material which is selected from a group including silicone, latex, urethane, and other flexible polymers, as commonly used in medical devices.

In operation, a conventional laparoscopic trocar (not shown) is initially placed through the skin. The RF device 10 is then applied through the laparoscopic trocar such that the RF device 10 enters the open body cavity. Note that in the foregoing step, the multi-lumen tube 14 is in its retracted position (see FIG. 1).

As shown in FIG. 2, the multi-lumen tube 14 is then extended from the outer sheath 12. Turning now to FIG. 3, the balloon member 18 is fully inflated with air or liquid so as to assume its expanded configuration. As the balloon member 18 inflates, the electrode needles 22 move toward their deployed configuration. The array of electrode needles 22 is now placed into the target tissue. Voltage is then supplied to the electrode needles 22 such that RF energy is emitted therefrom to the tissues surrounding each of the electrode needles 22. After a predetermined time period between 5 and 50 minutes, preferably 15 minutes, the power to the electrode needles 22 is terminated. Next, the RF device 10 is removed from the target tissue and moved to a second treatment zone or from the body cavity by initially deflating the balloon member 18 into its collapsed configuration such that the electrode needles 22 assume their compressed configuration, and then retracting the multi-lumen tube 14 into the outer sheath 12. Lastly, the device is removed from the body through the trocar.

As is evident from the description above, the present invention provides numerous advantages. For instance, because each of the electrode needles 22 extends in a substantially parallel relationship relative to the other electrode needles 22 as shown in FIG. 3, the heating and electric fields will be homogenous along the length of the electrode needles 22. Only the desired penetration depth is used since the electrode needles 22 can be inserted into tissue between 5 and 50 mm, preferably 30 mm. Further, the RF device 10 provides a more predictable heating than that of competitive devices. The RF device 10 can thermally treat malignant or benign pathologies without requiring surgery. The electrode needles 22 can be arranged such that the radius of the deployed array has a length such that the heating takes place between the electrode needles 22, when configured in a bipolar fashion, with alternating polarity between adjacent needles. This radius could be 1 cm if the electrode needles 22 are spaced 1 to 3 mm apart, and any larger radius (1.5 to 3 cm) with the same spaced apart configuration would have the same effect. In summary, with this configuration, only the outside of the treatment area is heated such that a cylindrical shell of volume of necrosis is created.

A second exemplary embodiment of the present invention is illustrated in FIGS. 6 to 10c. Elements illustrated in FIGS. 6 to 10c which correspond to the elements described above with reference to FIG. 1 have been designated by corresponding reference numerals increased by one hundred. In addition, elements illustrated in FIGS. 6 to 10c which do not correspond to the elements described above with reference to FIG. 1 have been designated by odd numbered reference numerals starting with reference number 111. The embodiment of FIGS. 6 to 10c operates in the same manner as the embodiment of FIG. 1, unless it is otherwise stated.

Figures 6, 7:
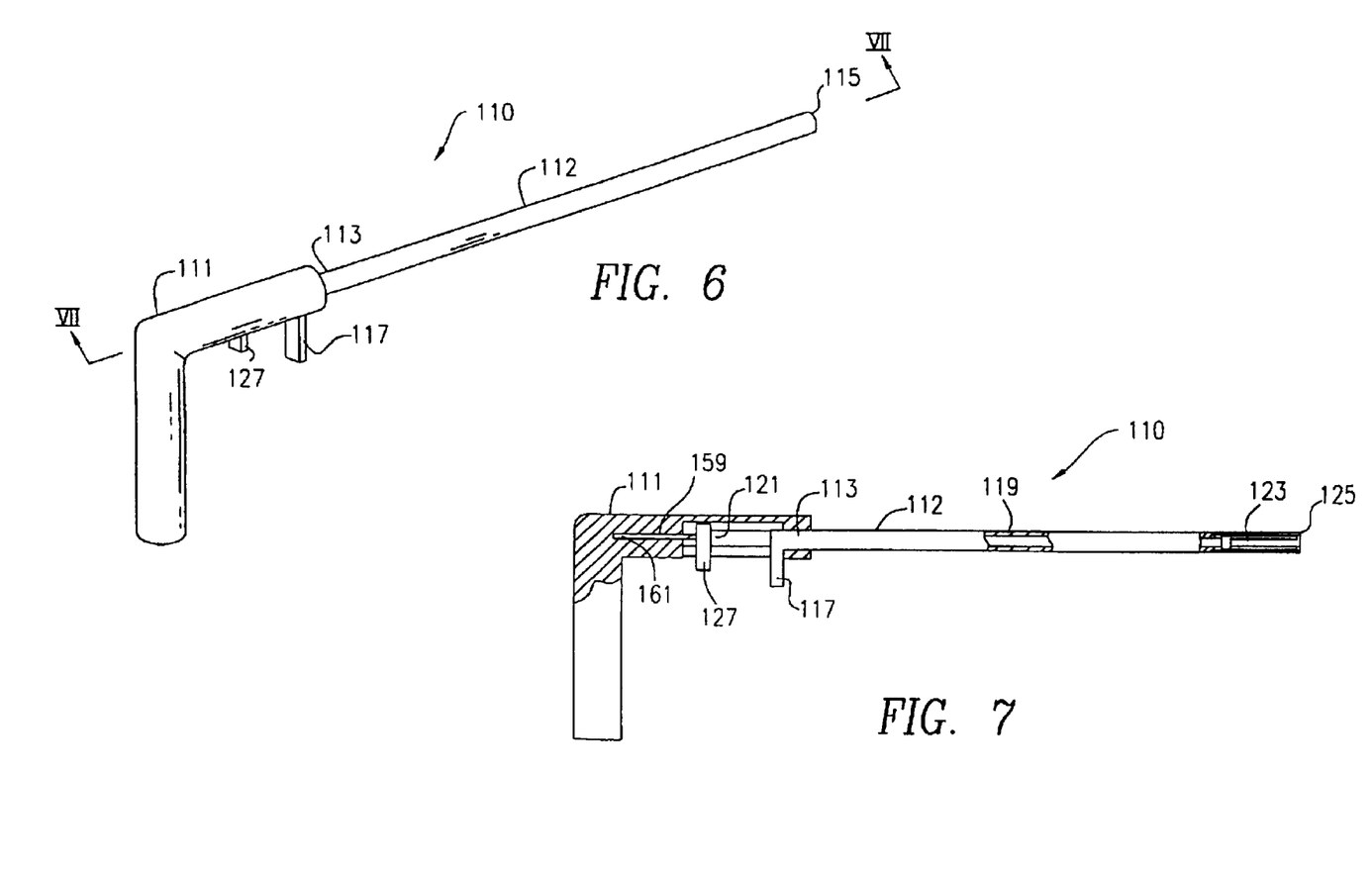
FIG. 6 is a front, perspective view of an RF device constructed in accordance with a second embodiment of the present invention, which shows a sleeve in an extended position.
FIG. 7 is a cross-sectional view, taken along section lines VII—VII and looking in the direction of the arrows, of the RF device of FIG. 6.

FIG. 6 shows an RF device 110 having a handle portion 111 and an elongated sleeve 112 attached thereto. The elongated sleeve 112 includes a proximal end 113 received within the handle portion 111 and a distal end 115 sized and shaped to be received within the target tissue for reasons described hereinafter. A finger gripping flange 117 is located at the proximal end 113 of the sleeve 112, for moving the sleeve 112 between a retracted position (see FIG. 8) and an extended position (see FIG. 6), as will be described below.

Referring to FIG. 7, the RF device 110 also includes a probe sheath 119 coaxially received within the sleeve 112. The probe sheath 119 includes a proximal end 121 received within the handle portion 111, a distal portion 123, and a distal end 125 sized and shaped to be received within the target tissue for reasons described hereinafter. A flange 127 is located at the proximal end 121 of the probe sheath 119 and utilized to move the probe sheath 119 between a retracted position (see FIG. 9) and an extended position (see FIG. 6), as will be described below.

Figures 9, 9A:
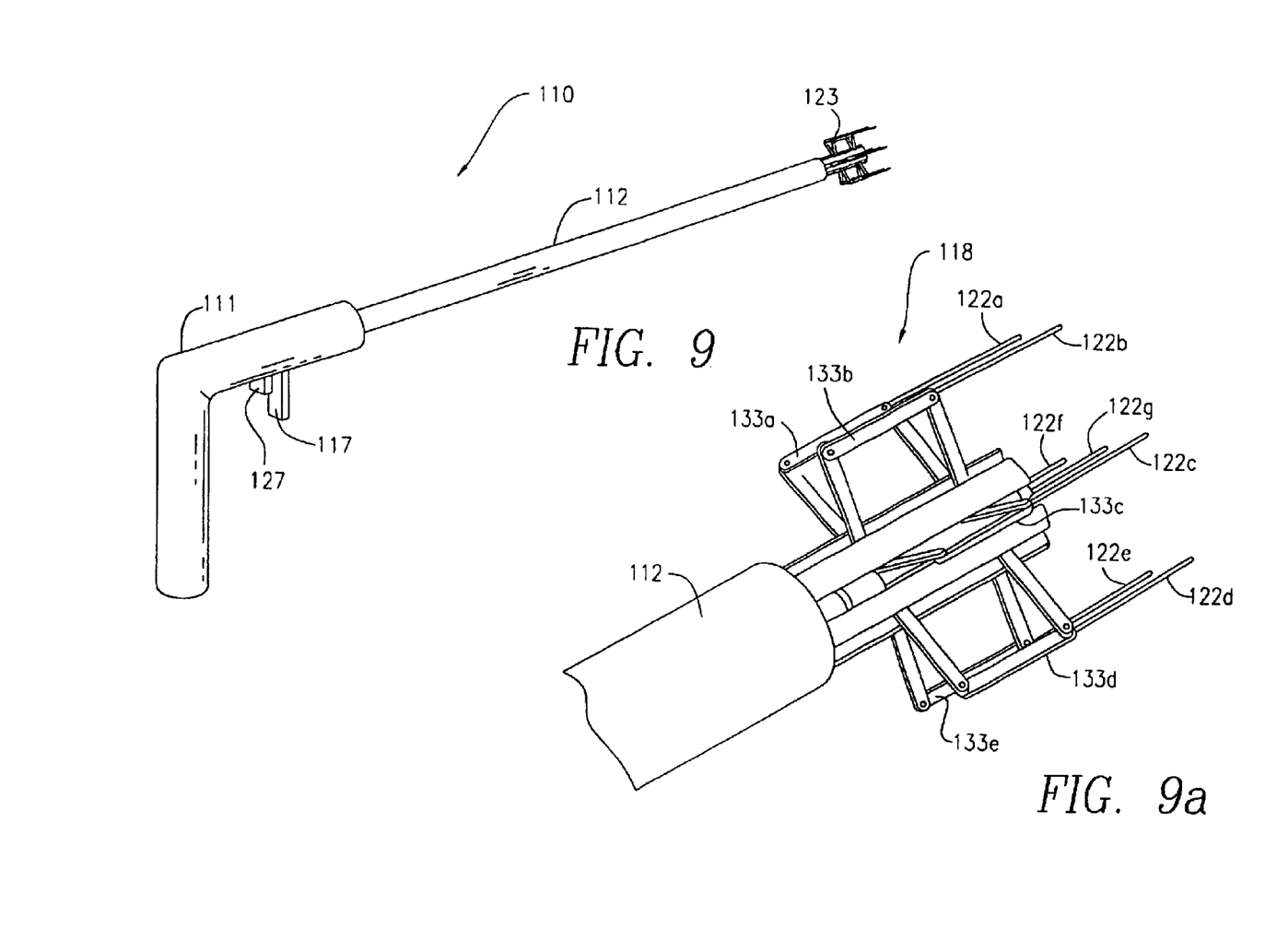
FIG. 9 is a view similar to the view shown in FIG. 8, except that the arms are in an expanded configuration.
FIG. 9a is an exploded view of the distal portion of the RF device of FIG. 9.
Figure 9B:
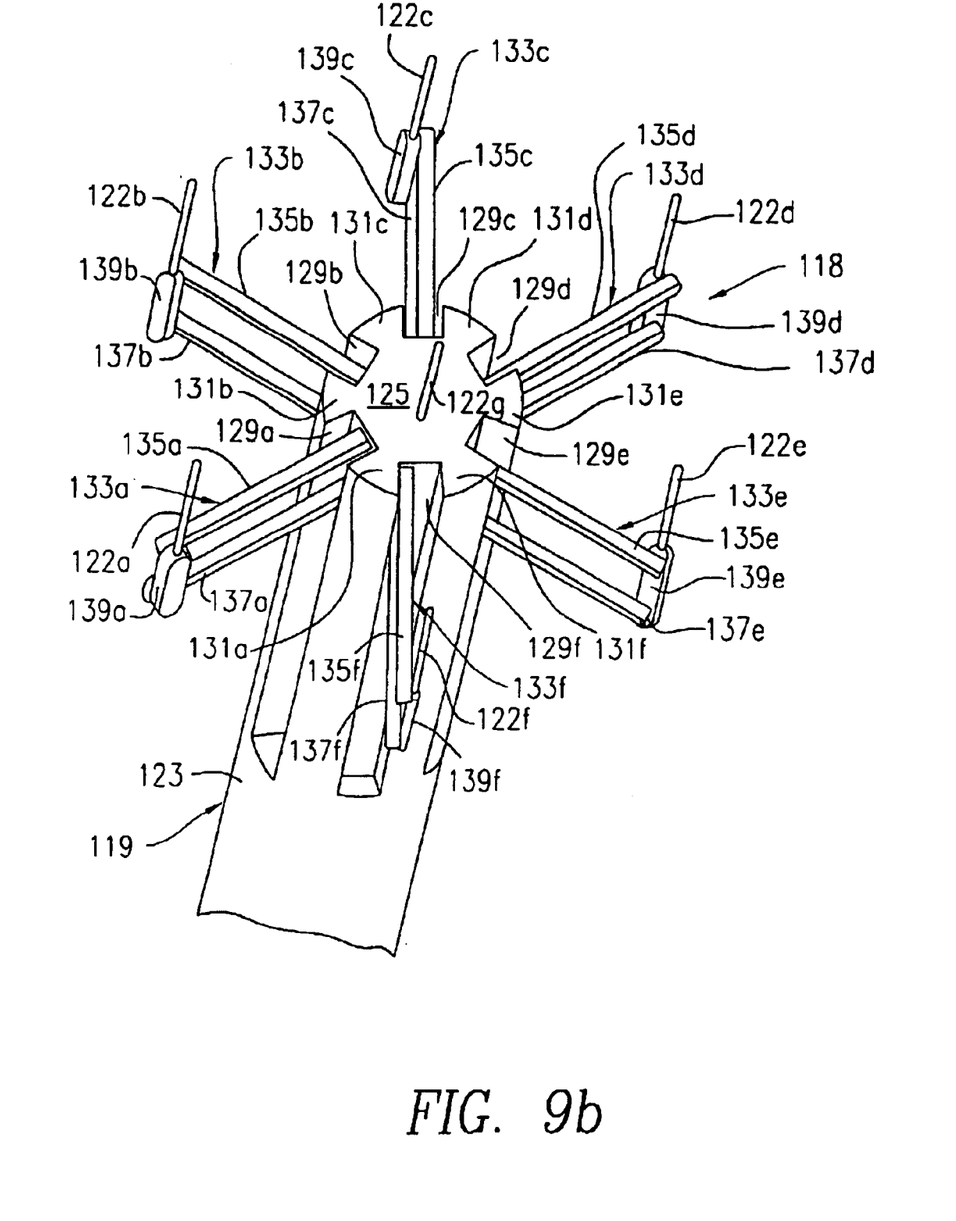

With reference to FIG. 9B, the distal portion 123 of the probe sheath 119 has six longitudinal grooves 129a–f on its outer surface so as to form six longitudinally extending bars 131a–f. The longitudinal groove 129a is formed between an adjacent pair of the bars 131a–b, while the longitudinal groove 129b is formed between an adjacent pair of the bars 131b–c. Also, the longitudinal groove 129c is formed between an adjacent pair of the bars 131c–d, while the longitudinal groove 129d is formed between an adjacent pair of the bars 131d–e. The longitudinal groove 129e is formed between an adjacent pair of the bars 131e–f, while the longitudinal groove 129f is formed between an adjacent pair of the bars 131f–a.

Referring still to FIG. 9B, an expandable member 118 is provided and includes six arms 133a–f, each of which is expandable between a collapsed configuration (see FIG. 8a) and an expanded configuration (see FIG. 9a) as will be described in further detail hereinafter. A plurality of generally linearly shaped electrode needles 122a–f is provided for delivering RF energy. More particularly, the needles 122a–f are attached to the arms 133a–f, respectively, by conventional attaching means. The polarity of the electrode needles 122a–f can be regulated such that each of the electrode needles 122a–f can be activated in various arrangements to be used as an active or return electrode. For example, the three adjacent electrode needles 122a, 122b, 122c may be active and the remaining three electrode needles 122d, 122e, 122f may be return. Alternatively, adjacent electrode needles (e.g., 122a, 122b) may be active and return, making an alternating pattern. Alternatively, all of the electrode needles 122a–f may be active and the return is a ground pad on the patient (not shown).

With reference to FIG. 9b, the arms 133a–f includes front sections 135a–f, back sections 137a–f, needle sections 139a–f, and side sections (see FIGS. 10a–c) (only side sections 141a, 141d are visible in FIGS. 10a–c), respectively. The electrode needles 122a–f are attached to the needle sections 139a–f, respectively. For simplicity, only two of the arms 133a, 133d are described in detail below with reference to FIGS. 10a–c. It will be understood that the structure and operation of all of the arms 133a–f are similar. Adjacent sections are hingedly attached to each other. More particularly, with reference to FIG. 10c, the front section 135a is hingedly attached to the needle section 139a at a first joint 143a along one edge of the front section 135a, and to the side section 141a at a second joint 145a along an opposite edge of the front section 135a. The needle section 139a is hingedly attached to the front section 135a at the first joint 143a along one edge of the needle section 139a, and to the back section 137a at a third joint 147a along an opposite edge of the needle section 139a. Likewise, the back section 137a is hingedly attached to the needle section 139a at the third joint 147a along one edge of the back section 137a, and to the side section 141a at a fourth joint 149a along an opposite edge of the back section 137a. The side section 141a is hingedly attached to the back section 137a at the fourth joint 149a along one edge of the side section 141a, and to the front section 135a at the second joint 145a along an opposite edge of the side section 141a. Similarly, the front section 135d is hingedly attached to the needle section 139d along one edge of the front section 135a, and to the side section 141d along an opposite edge of the front section 135d. The needle section 139d is hingedly attached to the front section 135d along one edge of the needle section 139d, and to the back section 137d along an opposite edge of the needle section 139d. Likewise, the back section 137d is hingedly attached to the needle section 139d along one edge of the back section 137d, and to the side section 141d along an opposite edge of the back section 137d. The side section 141d is hingedly attached to the back section 137d along one edge of the side section 141d, and to the front section 135d along an opposite edge of the side section 141d.

The second joint (e.g., 145a) of each of the arms 133a–f has an opening (not shown) through which conventional attaching means pass through so as to connect all of the side sections of the arms 133a–f along one edge of each side section. Likewise, the fourth joint (e.g., 149a) of each of the arms 133a–f has an opening (not shown) through which conventional attaching means pass through so as to connect all of the side sections of the arms 133a–f along an opposite edge of each side section.

Figure 10A:
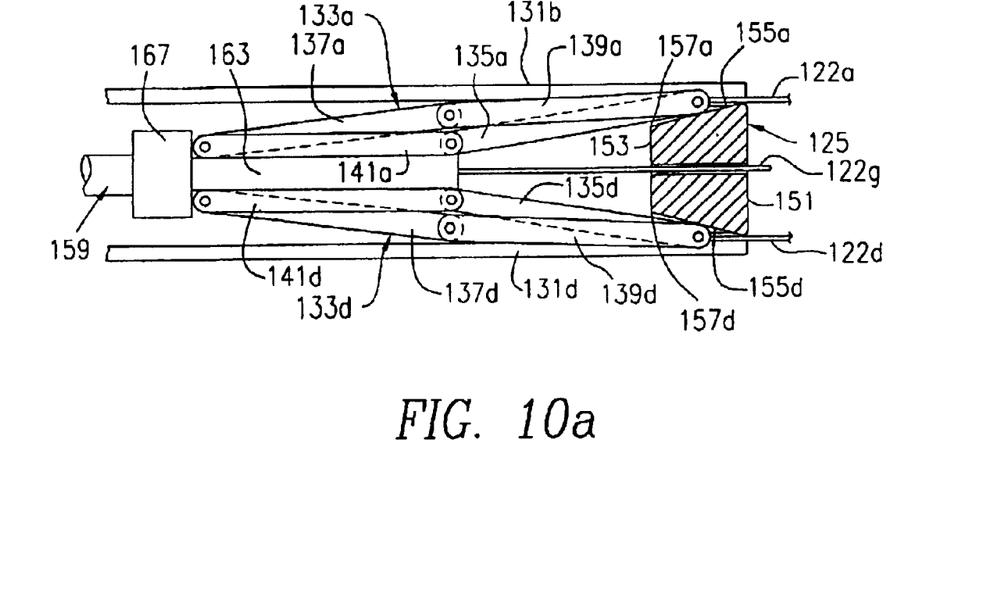
FIGS. 10a–c are sequential, partial cross-sectional views, showing the progressive movement of two of the arms as they move from the collapsed configuration to the expanded configuration.
Figure 10B:
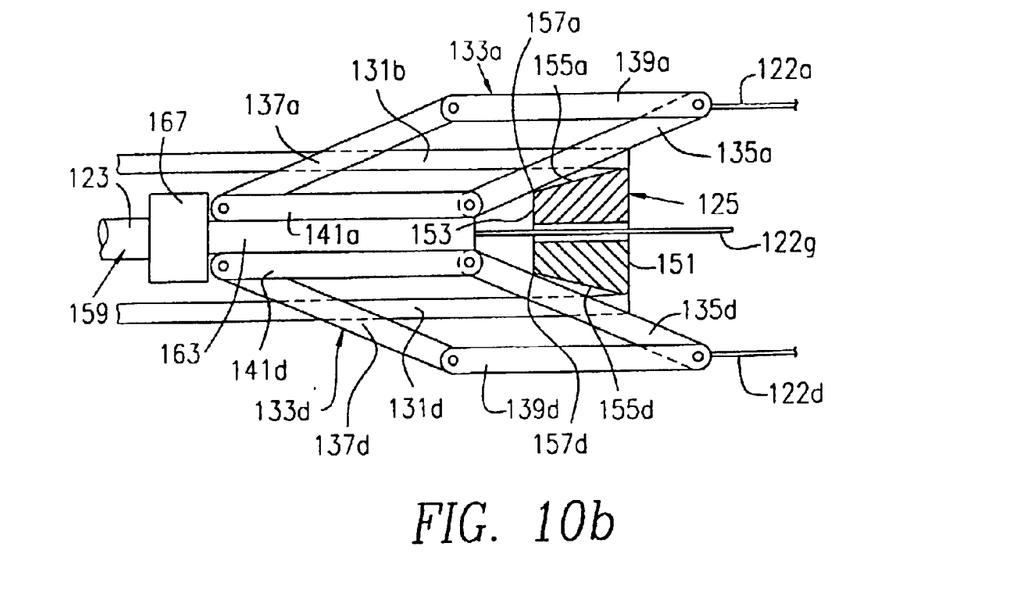
Figure 10C:
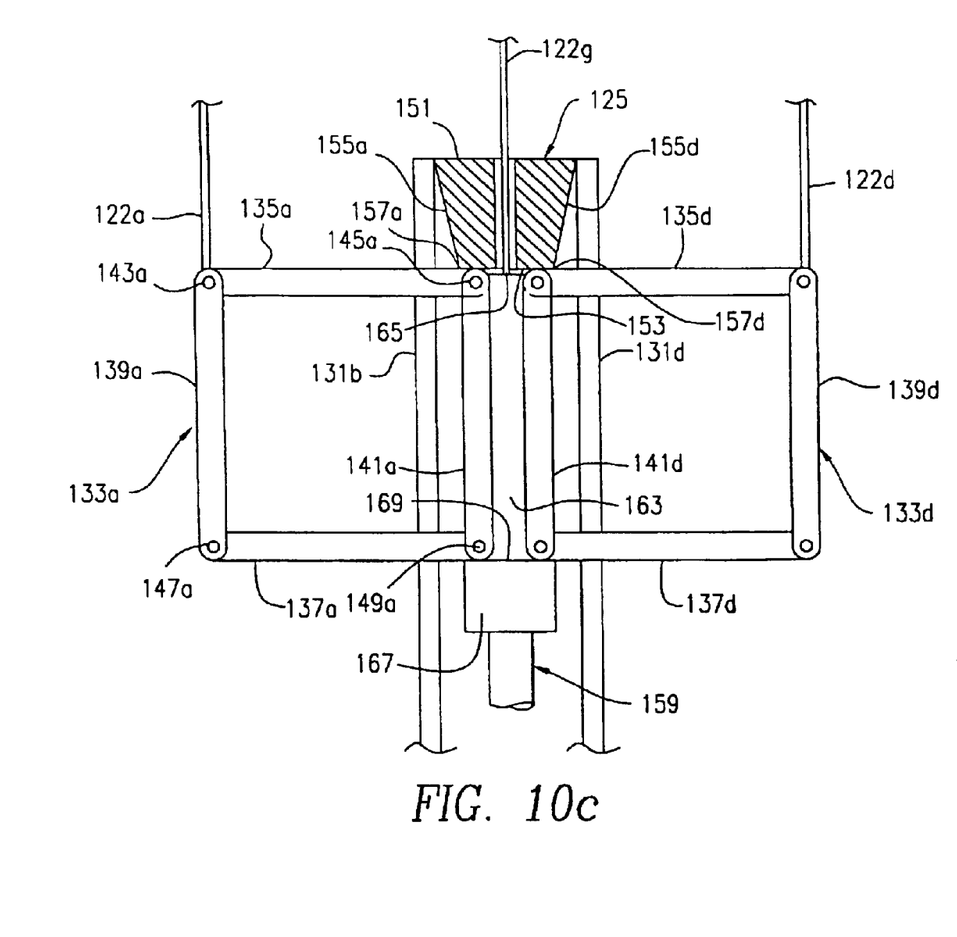

Referring to FIGS. 10a–c, the distal end 125 of the probe sheath 119 includes a front portion 151, a back portion 153, and six inwardly tapered sides (only opposing sides 155a, 155d are visible in FIGS. 10a–c) located within the six longitudinal grooves 129a–f (see FIG. 9B), respectively. The back portion 153 is attached to the six inwardly tapered sides along a circumferential edge (only two edge points 157a, 157d of which are visible in FIGS. 10a–c).

Referring back to FIG. 7, the RF device 110 further includes an elongated tube 159 coaxially received within the probe sheath 119. The elongated tube 159 has a proximal end 161 received within the handle portion 111 and a distal portion 163 (see FIGS. 10a–c) sized and shaped to be received within the target tissue. With reference to FIGS. 10a–c, the distal portion 163 of the elongated tube 159 is located between the six arms 133a–f (only the arms 133a, 133d are visible). The RF device 110 also includes an electrode needle 122g attached to an end 165 of the distal portion 163. The elongated tube 159 also includes a cylindrical member 167 connected to an opposite end 169 of the distal portion 163 and connected to the arms 133a–f of the expandable member 118.

In operation, a conventional laparoscopic trocar (not shown) is initially placed through the skin in some cases. Alternatively, a percutaneous approach may be used. The RF device 110 is then applied through the laparoscopic trocar such that the RF device 110 enters the open body cavity. Note that in the foregoing step, the sleeve 112 is in its extended position (see FIG. 6), in which the sleeve 112 covers the probe sheath 119 and the arms 133a–f.

Figures 8, 8A:
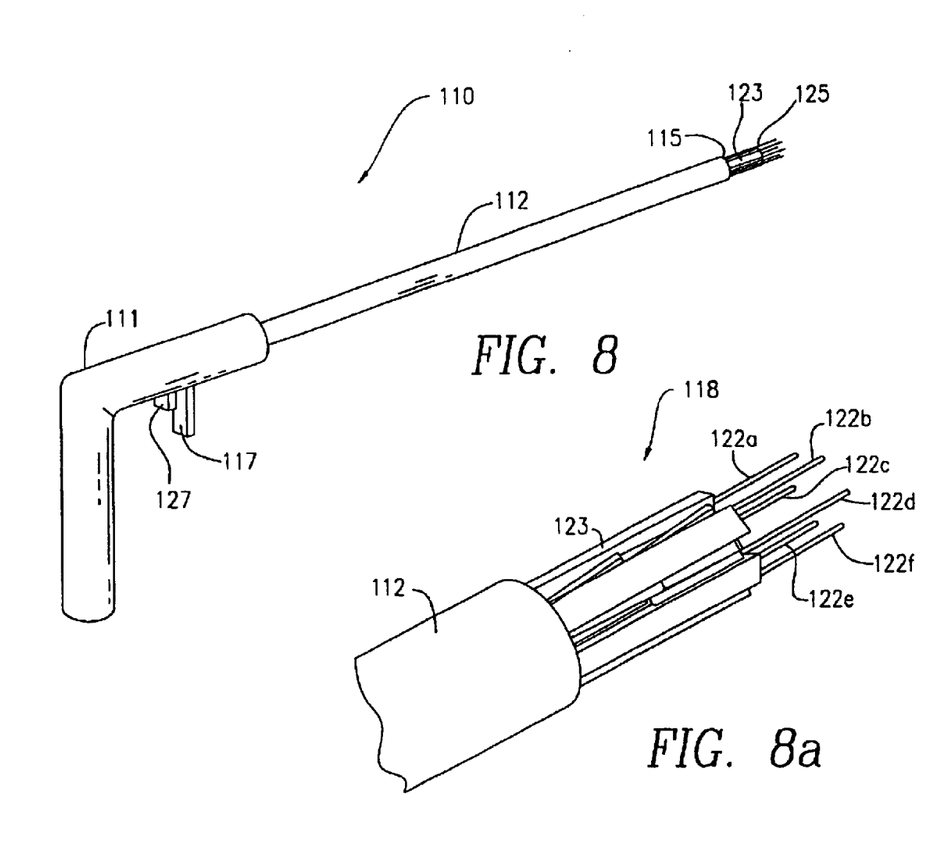
FIG. 8 is a view similar to the view shown in FIG. 6, except that the sleeve is in a retracted position and a plurality of arms is in a collapsed configuration.
FIG. 8a is an exploded view of the distal portion of the RF device of FIG. 8.

As shown in FIGS. 8 and 8a, the finger gripping flange 117 (see FIG. 8) is retracted such that the sleeve 112 moves in a proximal direction toward the handle portion 111 until it is in contact with the flange 127 of the probe sheath 119 so as to expose the distal portion 123 of the probe sheath 119 and the arms 133a–f. Turning now to FIGS. 9 and 9a, the finger gripping flange 117 is further retracted so as to cause the flange 127 to retract toward the handle portion 111. As the flange 127 retracts, the probe sheath 119 moves from its extended position to its retracted position, such that each of the arms 133a–f deploys to its expanded configuration as will be described in further detail hereinafter.

The following description will describe the deployment of the arms (only the arms 133a, 133d are visible in FIGS. 10a–c), i.e., to make the conversion from the collapsed configuration illustrated in FIG. 10a to the expanded configuration illustrated in FIG. 10c. Initially as illustrated in FIG. 10a, the front section 135a is positioned so as to rest on the side 155a of the distal end 125 of the probe sheath 119. In this position, the front section 135a is adjacent to and substantially parallel to the needle section 139a, and the side section 141a is adjacent to and substantially parallel to the back section 137a. As shown in FIG. 10b, as the flange 127 (see FIG. 9) retracts, the distal end 125 of the probe sheath 119 retracts such that contact between the front section 135a and the edge point 157a of the distal end 125 allows the front section 135a to pivot about pivot points 143a, 145a. As the front section 135a pivots, the needle section 139a and the back section 137a also pivot. When the pivot point 145a contacts the edge point 157a, the arm 133a is in its expanded configuration such that adjacent sections (e.g., 135a, 139a) are substantially perpendicular to each other.

RF energy is then supplied to the electrode needles 122a–g such that RF energy is emitted therefrom to the tissues surrounding each of the electrode needles 122a–g. After a predetermined time period between 5 and 50 minutes, preferably 15 minutes, the power to the electrode needles 122a–g is terminated. Next, the RF device 110 is removed from the target tissue and to the second target location or from the body cavity by extending the finger gripping flange 117 toward the arms 133a–f such that contact between the sleeve 112 and the back section (e.g., 137a) of each of the arms 133a–f moves the arms 133a–f into their collapsed configuration. Lastly, the RF device 110 is removed from the body through the trocar.

Figure 11:
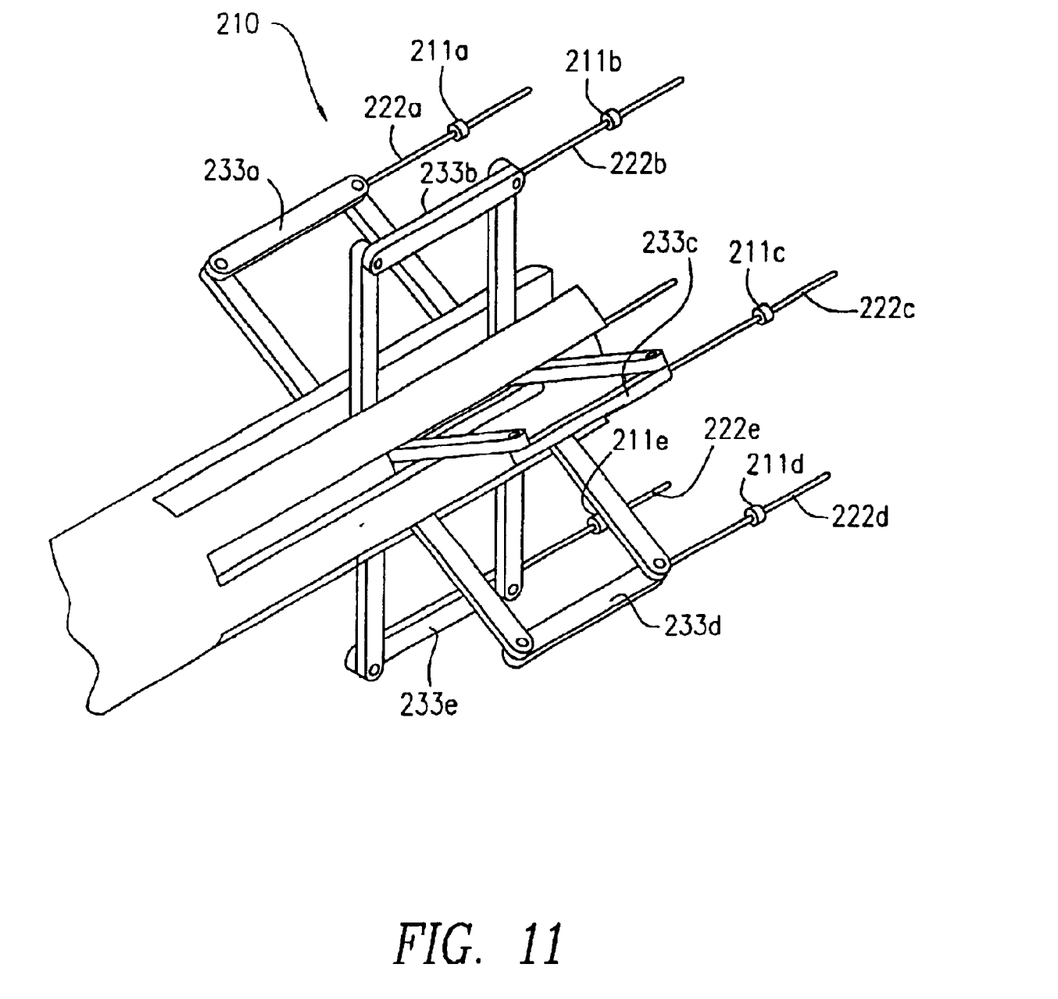
FIG. 11 is a front, perspective view of a distal portion of an RF device constructed in accordance with a third embodiment of the present invention.

A third exemplary embodiment of the present invention is illustrated in FIG. 11. Elements illustrated in FIG. 11 which correspond to the elements described above with reference to FIGS. 6 to 10c have been designated by corresponding reference numerals increased by one hundred. In addition, elements illustrated in FIG. 11 which do not correspond to the elements described above with reference to FIGS. 6 to 10c have been designated by odd numbered reference numerals starting with reference number 211. The embodiment of FIG. 11 operates in the same manner as the embodiment of FIGS. 6 to 10c, unless it is otherwise stated.

FIG. 11 shows an RF device 210 having six movable parts 211a–e (only five of which are shown) attached to the six needles 222a–e (only five of which are shown), respectively, of the arms 233a–e. The movable parts 211a–e are electrically connected to the six needles 222a–e, respectively, and may be cylindrical, spherical, hemispherical, etc. In operation, the needles 222a–e are inserted into tissue to the desired depth, which is in a range of approximately 1 to 4 cm. Then, the needles 222a–e are inserted further, about 2 to 4 mm, into the tissue and then withdrawn 2 to 4 mm. In this position, the movable parts 211a–e are 2 to 4 mm away from the tissue surface. Once the needles 222a–e are activated, the tissue is heated and the power is shut off. Then, the needles 222a–e are advanced 2 to 4 mm such that the movable parts 211a–e are in contact with the tissue surface. Power is switched on again and the movable parts 211a–e heat the tissue at the interface. After approximately 5 to 10 seconds of activation, the tissue interface is sufficiently coagulated. The purpose of the movable parts 211a–e is to stop any bleeding at the location where the needles 222a–e enter the tissue.

It should be noted that the RF device 10, 110, 210 can have numerous modifications and variations. For instance, the RF device 10, 110, 210 can be either disposable or non-disposable. The RF device 10, 110, 210 can have laparoscopic applications and can be used to treat various sites such as the liver, kidney, spine, lung, and fibroids on or in the wall of the uterus. Also, the RF device 10, 110, 210 can have percutaneous applications and can be used to treat various sites such as the breast and the prostate. The electrode needles 22a–d, 122a–g, 222a–e can be insulated in sections to regulate the conductive portion and the heating field. In such aspects, RF current will flow only through the needle portion that is not covered by insulation. The RF device 10, 110, 210 can employ alternative energy sources such as laser fibers, ultrasound PZT based cylinders, chemical, microwave antennas, and/or a cryogenic device. The foregoing energy sources can include either catheters or needles. It will be understood that although seven electrode needles 122 are shown in FIG. 9b, the number of electrode needles 122 can vary. Likewise, although six longitudinal grooves 129a–f and six longitudinally extending bars 131a–f are shown, the number of grooves 129a–f and bars 131a–f can vary. All such variations and modifications are intended to be included within the scope of the invention as defined in the appended claims.

What is claimed is:

1. A medical device used for thermal treatment of tissue, comprising an elongated probe sheath having a longitudinal axis; an expandable member attached to said elongated probe sheath, said expandable member being expandable from a collapsed configuration to an expanded configuration; and a plurality of energy-emitting electrodes attached to said expandable member such that each of said electrodes is arranged generally coaxially relative to said probe sheath when said expandable member is in its said collapsed and expanded configurations, said expandable member including a plurality of arms, each of said arms being expandable between a collapsed configuration and an expanded configuration, said probe sheath including a plurality of inwardly tapered sides in cooperation with said arms, and said probe sheath being movable between a retracted position and an extended position.

2. The medical device of claim 1, further comprising a sleeve sized and shaped so as to receive said probe sheath and said expandable member when said expandable member is in its said collapsed configuration.

3. The medical device of claim 2, wherein each of said electrodes moves radially outward from said probe sheath as said expandable member moves from its said collapsed configuration to its said expanded configuration.

4. The medical device of claim 3, wherein said electrodes are in close proximity to each other when said expandable member is in its said collapsed configuration and wherein said electrodes are spaced apart from each other when said expandable member is in its said expanded configuration.

5. The medical device of claim 4, wherein said probe sheath extends completely through said expandable member, whereby said expandable member is positioned along an intermediate length of said probe sheath.

6. The medical device of claim 5, wherein each of said electrodes has a generally linear shape.

7. The medical device of claim 6, wherein said probe sheath is movable between a retracted position, in which said probe sheath retracts into said sleeve, and an extended position, in which said probe sheath extends axially outward from said sheath.

8. The medical device of claim 7, wherein said tube includes a plurality of channels, at least one of said channels being sized and shaped so as to allow a fluid to pass therethrough.

9. The medical device of claim 8, wherein said expandable member is expandable to its said expanded configuration when a fluid is passed through said at least one of said channels.

10. The medical device of claim 9, wherein said expandable member is collapsible to its said collapsed configuration when a vacuum is supplied to said expandable member through at least another of said channels.

11. The medical device of claim 10, further comprising a plurality of wire leads connected to said electrodes.

12. The medical device of claim 11, wherein at least another of said channels is sized and shaped to allow said wire leads to pass therethrough.

13. The medical device of claim 12, wherein said expandable member is a balloon member.

14. The medical device of claim 13, wherein said electrodes emit RF energy.

15. The medical device of claim 14, wherein said balloon member is substantially cylindrically-shaped when it is in its said expanded configuration.

16. The medical device of claim 15, wherein said electrodes surround said tube when said balloon member is in its expanded configuration.

17. The medical device of claim 16, wherein said expandable member is attached to said tube by a solvent-based glue.

18. A method for performing thermal treatment of tissue using a medical device which includes a probe sheath having a plurality of inwardly tapered sides, an expandable member including a plurality of arms, the expandable member attached to the tube and expandable from a collapsed configuration to an expanded configuration, and a plurality of electrodes attached to the expandable member, said method comprising the steps of:

(a) inserting the medical device within a tissue area with the expandable member in its collapsed configuration, in which the electrodes are in close proximity to each other and in which all of the electrodes are arranged generally coaxially relative to the probe sheath; and (b) moving the arms relative to the inwardly tapered sides of the probe sheath so as to expand the expandable member so that it assumes its expanded configuration, in which the electrodes are spaced apart from each other and in which all of the electrodes are arranged generally coaxially relative to the probe sheath.

19. The method of claim 18, wherein the method is used in a laparoscopic application.

20. The method of claim 18, wherein the method is used in a percutaneous application.

21. The medical device of claim 1, wherein each of said arms moves toward its said expanded configuration as said probe sheath moves from its said extended position to its said retracted position.

22. The medical device of claim 21, further comprising an elongated sleeve coaxially received over said probe sheath, said sleeve being movable between a retracted position and an extended position.

23. The medical device of claim 22, wherein each of said arms moves toward its said collapsed configuration as said sleeve moves from its said retracted position to its said extended position.

24. The medical device of claim 23, wherein the polarity of said electrodes can be selectively varied.

25. A medical device used for thermal treatment of tissue, comprising an elongated probe sheath having a longitudinal axis; an expandable member attached to said elongated probe sheath, said expandable member being expandable from a collapsed configuration to an expanded configuration; and a plurality of energy-emitting electrodes attached to said expandable member such that each of said electrodes is arranged generally coaxially relative to said probe sheath when said expandable member is in its said collapsed and expanded configurations, said expandable member including a plurality of arms, each of said arms being expandable between a collapsed configuration and an expanded configuration, said arms including a plurality of members connected to said electrodes, each of said members movable relative to said electrodes.

* * * * *